(12) United States Patent
Makino et al.

(10) Patent No.: US 10,659,658 B2
(45) Date of Patent: May 19, 2020

(54) PROCESSOR FOR ELECTRONIC ENDOSCOPE, AND ELECTRONIC ENDOSCOPE SYSTEM

(71) Applicant: HOYA CORPORATION, Tokyo (JP)

(72) Inventors: Takao Makino, Tokyo (JP); Yousuke Ikemoto, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 16/308,445

(22) PCT Filed: Aug. 30, 2017

(86) PCT No.: PCT/JP2017/031126
§ 371 (c)(1),
(2) Date: Dec. 7, 2018

(87) PCT Pub. No.: WO2018/043552
PCT Pub. Date: Mar. 8, 2018

(65) Prior Publication Data
US 2019/0273840 A1    Sep. 5, 2019

(30) Foreign Application Priority Data

Aug. 31, 2016   (JP) .................... 2016-169233

(51) Int. Cl.
*H04N 1/60*   (2006.01)
*A61B 1/00*   (2006.01)
(Continued)

(52) U.S. Cl.
CPC .......... *H04N 1/60* (2013.01); *A61B 1/00009* (2013.01); *A61B 1/045* (2013.01); *A61B 1/05* (2013.01);
(Continued)

(58) Field of Classification Search
None
See application file for complete search history.

(56) References Cited

U.S. PATENT DOCUMENTS

2010/0039507 A1* 2/2010 Imade ................ A61B 1/00165
                                                                  348/68
2013/0051642 A1   2/2013 Kanda et al.
(Continued)

FOREIGN PATENT DOCUMENTS

| JP | 2010-115243 A | 5/2010 |
|---|---|---|
| JP | 2012-152284 A | 8/2012 |

(Continued)

OTHER PUBLICATIONS

PCT/JP2017/031126, International Search Report, dated Oct. 3, 2017, 2 pages.

*Primary Examiner* — Eileen M Adams
(74) *Attorney, Agent, or Firm* — Kilpatrick Townsend & Stockton LLP (57) ABSTRACT

An electronic endoscope processor has a configuration including: a converting means for converting pieces of pixel data that are made up of n (n≥3) types of color components and constitute a color image in a body cavity into pieces of pixel data that are made up of m (m≥2) types of color components, m being smaller than n; a color component correcting means for correcting the converted pieces of pixel data made up of m types of color components with use of a predetermined color component correction coefficient; and an acquiring means for acquiring an evaluation result related to a target illness based on the corrected pieces of pixel data made up of m types of color components.

20 Claims, 6 Drawing Sheets

(51) Int. Cl.
  *A61B 1/05*    (2006.01)
  *G06T 3/00*    (2006.01)
  *H04N 1/64*    (2006.01)
  *A61B 1/045*   (2006.01)
  *G06T 1/60*    (2006.01)
  *G06T 1/00*    (2006.01)
  *A61B 5/00*    (2006.01)

(52) U.S. Cl.
  CPC ............... *A61B 5/00* (2013.01); *G06T 1/00* (2013.01); *G06T 1/60* (2013.01); *G06T 3/0006* (2013.01); *H04N 1/6008* (2013.01); *H04N 1/644* (2013.01)

(56) References Cited

U.S. PATENT DOCUMENTS

| | | | |
|---|---|---|---|
| 2014/0320620 A1 | 10/2014 | Ikemoto et al. | |
| 2015/0109492 A1* | 4/2015 | Hayashi | H04N 9/045 |
| | | | 348/277 |
| 2015/0181185 A1 | 6/2015 | Ikemoto et al. | |

FOREIGN PATENT DOCUMENTS

| | | |
|---|---|---|
| JP | 2014-018333 A | 2/2014 |
| JP | 2014-213094 A | 11/2014 |
| JP | 2016-077756 A | 5/2016 |

\* cited by examiner

PROCESSOR FOR ELECTRONIC ENDOSCOPE, AND ELECTRONIC ENDOSCOPE SYSTEM

CROSS-REFERENCE TO RELATED APPLICATIONS

This application is a 371 U.S. National Phase of PCT International Application No. PCT/JP2017/031126, filed on Aug. 30, 2017, which claims benefit and priority to Japanese patent application No. 2016-169233, filed on Aug. 31, 2016, and which is incorporated by reference herein in its entirety.

TECHNICAL FIELD

The present disclosure relates to an electronic endoscope processor and an electronic endoscope system.

BACKGROUND ART

An electronic endoscope system is used for observation and treatment inside a human body. When endoscopic observation is performed using an electronic endoscope system, it is necessary to accurately identify lesion sites and normal sites. A lesion site often has a different color tone from a normal site due to angiogenesis or the like. Patent Document 1 discloses an electronic endoscope system that includes a function for assisting endoscopic image diagnosis by specifying a site that has a high likelihood of being a lesion site based on color information in an endoscopic image, and displaying the specified site in an emphasized manner.

In order to accurately specify a lesion site or the like based on color information in an endoscopic image as described above, it is necessary to acquire an endoscopic image that has accurate color information at least in the color region used when specifying the lesion site or the like. Conventional electronic endoscope systems include a white balance correction function as a function for correcting color information in an endoscopic image.

CITATION LIST

Patent Document

[Patent Document 1] JP 2010-115243A

SUMMARY OF DISCLOSURE

Technical Problem

White balance correction is for performing color correction for only one point (e.g., white) on an achromatic color axis, and cannot correct chromatic color errors. For this reason, with conventional electronic endoscope systems that include only a white balance correction function as a function for correcting color information, large errors exist in the color information, and this causes low precision when identifying a lesion site or the like.

The present disclosure was achieved in light of the circumstances described above, and an object of the present disclosure is to provide an electronic endoscope processor and an electronic endoscope system that are favorable to improving identification precision when identifying a lesion site or the like based on color components in an endoscopic image.

Solution to Problem

An electronic endoscope processor according to an embodiment of the present disclosure includes: a converting means for converting each of a plurality of pieces of pixel data that are made up of n ($n \geq 3$) types of color components and constitute a color image of a biological tissue in a body cavity into a piece of pixel data that is made up of m ($m \geq 2$) types of color components, m being smaller than n; a color component correcting means for correcting the converted pieces of pixel data made up of m types of color components with use of a predetermined color component correction coefficient; and an acquiring means for acquiring an evaluation result related to a target illness based on the corrected pieces of pixel data made up of m types of color components.

Also, an electronic endoscope processor according to an embodiment of the present disclosure includes: a converting means for converting each of a plurality of pieces of pixel data that are made up of n ($n \geq 3$) types of color components and constitute a color image of a biological tissue in a body cavity into a piece of pixel data that is made up of m ($m \geq 2$) types of color components, m being smaller than n; an acquiring means for acquiring an evaluation result related to a target illness based on the converted pieces of pixel data made up of m types of color components; and an evaluation result correcting means for correcting the acquired evaluation result with use of a predetermined evaluation result correction coefficient.

In other words, it is preferable that an electronic endoscope processor according to an embodiment of the present disclosure includes:

a converting means for converting each of a plurality of pieces of pixel data that are made up of n ($n \geq 3$) types of color components and constitute a color image of a biological tissue in a body cavity into a piece of pixel data that is made up of m ($m \geq 2$) types of color components, m being smaller than n;

an acquiring means for acquiring an evaluation result related to a target illness based on the converted pieces of pixel data made up of m types of color components; and at least one correcting means out of a color component correcting means for correcting the pieces of pixel data that are made up of m types of color components and were converted by the converting means, with use of a predetermined color component correction coefficient, and an evaluation result correcting means for correcting the evaluation result acquired by the acquiring means, with use of a predetermined evaluation result correction coefficient.

In this configuration, according to an embodiment, it is preferable that the electronic endoscope processor further includes: a color component correcting means for correcting the pieces of pixel data made up of m types of color component with use of a predetermined color component correction coefficient. Also, in this case, according to an embodiment, it is preferable that the acquiring means acquires the evaluation result related to the target illness based on the pieces of pixel data that are made up of m types of color components and were corrected using the color component correction coefficient.

Also, according to an embodiment of the present disclosure, it is preferable that the color component correction coefficient is a predetermined correction matrix coefficient that corrects the pieces of pixel data made up of m types of color components, for example.

Also, according to an embodiment of the present disclosure, it is preferable that the evaluation result correction coefficient is an affine transformation coefficient that performs affine transformation on the evaluation result.

Also, according to an embodiment of the present disclosure, it is preferable that color components subjected to color correction performed by the color component correcting means are the m types of color components among the n types of color components, and do not include (n-m) types of color components.

Also, according to an embodiment of the present disclosure, it is preferable that the acquiring means sets a reference direction that is related to the target illness and extends from a predetermined reference point in a color space defined by the m types of color components, and, for each of a plurality of pixels of the color image, acquires the evaluation result related to the target illness based on an extent to which a direction from the reference point to a pixel correspondence point that corresponds to the converted piece of pixel data in the color space deviates from the reference direction.

Also, according to an embodiment of the present disclosure, it is preferable that the acquiring means sets a reference axis that is related to the target illness and passes through a predetermined reference point in a color plane defined by the m types of color components, and, for each of a plurality of pixels, acquires the evaluation result related to the target illness based on an angle formed by the reference axis and a line segment that connects the reference point and a pixel correspondence point corresponding to the piece of pixel data.

Also, according to an embodiment of the present disclosure, it is preferable that letting the reference axis be a first reference axis, the acquiring means sets a second reference axis that is related to a healthy site not having the target illness and that passes through the reference point in the color plane, and the angle θ is normalized with use of an intersecting angle of the first reference axis and the second reference axis as a maximum angle before the evaluation value is calculated.

Also, according to an embodiment of the present disclosure, it is preferable that the converting means orthographically projects, onto the color plane, the pieces of pixel data in a color space defined by the n types of color components.

Also, according to an embodiment of the present disclosure, it is preferable that the reference axis is an axis that indicates an inflamed site having the highest symptom level of the target illness, for example. In other words, it is preferable that the reference axis is an axis to which the converted pixel correspondence points increasingly converge as a symptom level of the target illness rises.

Also, according to an embodiment of the present disclosure, it is preferable that the color plane is a plane that includes an R component axis and a G component axis, for example.

Also, according to an embodiment of the present disclosure, it is preferable that the m types of color components of the converted pieces of pixel data are color components set so as to have mutually different wavelength bands.

Also, according to an embodiment of the present disclosure, it is preferable that the evaluation result includes at least one of a value indicating an evaluation related to the target illness, and a color image indicating an evaluation related to the target illness, for example.

Also, an electronic endoscope system according to an embodiment of the present disclosure includes any of the above electronic endoscope processors, and a color component correction coefficient calculating means for calculating a color component correction coefficient based on at least two or more types of real imaging data obtained by capturing images of at least two or more indicators related to a target illness.

Also, an electronic endoscope system according to an embodiment of the present disclosure includes any of the above electronic endoscope processors, and an evaluation result correction coefficient calculating means for acquiring an evaluation result for each of a plurality of indicators by capturing images of the indicators, and calculating an evaluation result correction coefficient with use of the acquired evaluation results of the indicators.

Also, an electronic endoscope system according to an embodiment of the present disclosure includes: any of the above electronic endoscope processors; and a display apparatus configured to display, on a display screen, an evaluation result obtained by the electronic endoscope processor.

Also, according to an embodiment of the present disclosure, it is preferable that the electronic endoscope processor includes: an acquiring means for acquiring a color map image by converting colors of pixels of the color image into colors that correspond to the evaluation values calculated as the evaluation results of the pixels; and a displaying means for displaying the color map image on the display screen of the display apparatus, and the display apparatus, which is a monitor for example, is configured to display a representative value of the evaluation values and the color map image at the same time for example.

Also, according to an embodiment of the present disclosure, hue and saturation are excluded from the color components.

Advantageous Effects of Disclosure

According to the electronic endoscope processor and the electronic endoscope system described above, it is possible to improve identification precision when identifying a lesion site or the like based on color components in an endoscopic image.

DESCRIPTION OF EMBODIMENTS

Hereinafter, embodiments of the present disclosure will be described with reference to the drawings. The following description is given taking the example of an electronic endoscope system as an embodiment of the present disclosure.

Figure 1:
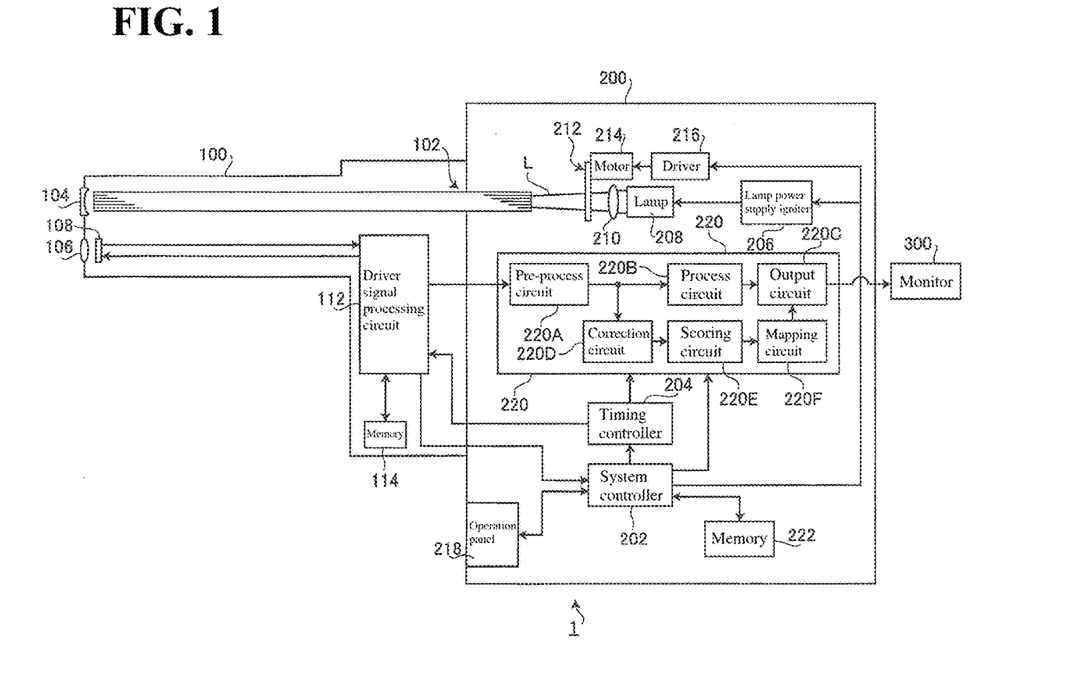
FIG. 1 is a block diagram showing a configuration of an electronic endoscope system according to an embodiment of the present disclosure.

FIG. 1 is a block diagram showing the configuration of an electronic endoscope system 1 according to an embodiment of the present disclosure. As shown in FIG. 1, the electronic endoscope system 1 is a system that is specialized for medical use, and includes an electronic endoscope 100, a processor 200, and a monitor 300.

The processor 200 includes a system controller 202 and a timing controller 204. The system controller 202 executes various programs that are stored in a memory 222, and performs overall control of the electronic endoscope system 1. The system controller 202 is also connected to an operation panel 218. The system controller 202 changes operations of the electronic endoscope system 1 and parameters for operations in accordance with instructions from an operator that are received the operation panel 218. One example of such instructions input by the operator is an instruction for switching the operating mode of the electronic endoscope system 1. In the present embodiment, the operating modes include a normal mode, a special mode, and a calibration mode. The timing controller 204 outputs, to circuits in the electronic endoscope system 1, clock pulses for adjusting the timing of operations of various units.

After being started by a lamp power supply igniter 206, a lamp 208 emits white light L. The lamp 208 is a high-intensity lamp such as a xenon lamp, a halogen lamp, a mercury lamp, or a metal halide lamp. The white light L emitted by the lamp 208 is condensed by a condensing lens 210 and restricted to an appropriate light amount via a diaphragm 212. Note that the lamp 208 may be replaced with a semiconductor light emitting element such as an LD (Laser Diode) or an LED (Light Emitting Diode). A semiconductor light emitting element has features such as having a lower power consumption and smaller heat emission amount than other light sources, and therefore has an advantage of making it possible to acquire bright images while also suppressing power consumption and the heat emission amount. The ability to acquire bright images leads to an improvement in the precision of a later-described inflammation evaluation value. The semiconductor light emitting element is not limited to being provided in the processor 200, and may be provided in the electronic endoscope 100. For example, the semiconductor light emitting element may be provided in the distal end portion of the electronic endoscope 100.

A motor 214 is mechanically coupled to the diaphragm 212 via transmission mechanisms such as an arm and a gear, which are not shown. The motor 214 is a DC motor for example, and is driven under drive control of a driver 216. The diaphragm 212 is operated by the motor 214, and the opening degree is changed in order to set the images displayed on the display screen of a monitor 300 to an appropriate brightness. The light amount of the white light L emitted by the lamp 208 is limited according to the opening degree of the diaphragm 212. The appropriate image brightness reference is set and changed according to an intensity adjustment operation performed on the operation panel 218 by the operator. Note that the light control circuit for performing intensity adjustment by controlling the driver 216 is a known circuit and will not be described in this specification.

The white light L that passes through the diaphragm 212 is condensed on the entrance end face of an LCB (Light Carrying Bundle) 102 and enters the LCB 102. The white light L that entered the LCB 102 through the entrance end face propagates inside the LCB 102.

After propagating inside the LCB 102, the white light L exits through an exit end face of the LCB 102 arranged at the leading end of the electronic endoscope 100, passes through a light distribution lens 104, and illuminates biological tissue. Returning light from the biological tissue illuminated by the white light L passes through an objective lens 106 and forms an optical image on the light receiving surface of a solid-state image sensor 108.

The solid-state image sensor 108 is a single-plate color CCD (Charge Coupled Device) image sensor that has a complimentary color checkered filter. The solid-state image sensor 108 accumulates charge according to the light quantity of an optical image formed on pixels on the light receiving surface, generates yellow Ye, cyan Cy, green G, and magenta Mg pixel data, and outputs the pixel data. Note that the solid-state image sensor 108 is not limited to being a CCD image sensor, and may be replaced with a CMOS (Complementary Metal Oxide Semiconductor) image sensor or another type of imaging apparatus.

Also, the solid-state image sensor 108 may include a primary color filter (Bayer arrangement filter). A primary color (RGB) filter has better color development characteristics than a complementary color filter. For this reason, if an RGB-format image signal obtained by an image sensor that has a primary color filter is used to calculate a later-described inflammation evaluation value, it is possible to improve the precision of that evaluation. Also, using a primary color filter eliminates the need to perform signal conversion in the processing for calculating the inflammation evaluation value. This therefore makes it possible to suppress the processing load in inflammation evaluation value calculation.

A driver signal processing circuit 112 is provided in a connection portion of the electronic endoscope 100. Pixel data from pixels that captured biological tissue illuminated by white light L are input by the solid-state image sensor 108 to the driver signal processing circuit 112 at a frame cycle. The pixel data input from the solid-state image sensor 108 is output by the driver signal processing circuit 112 to a signal processing circuit 220 of the processor 200. Note that the term "frame" may be replaced with "field" in the following description. In the present embodiment, the frame cycle and the field cycle are respectively 1/30 seconds and 1/60 seconds.

The driver signal processing circuit 112 also accesses a memory 114 and reads out unique information regarding the electronic endoscope 100. The unique information regarding the electronic endoscope 100 recorded in the memory 114 includes, for example, the pixel count, sensitivity, operable frame rate, and model number of the solid-state image sensor 108. The unique information read out from the memory 114 is output by the driver signal processing circuit 112 to the system controller 202.

The system controller 202 generates control signals by performing various arithmetic operations based on the unique information regarding the electronic endoscope 100. The system controller 202 uses the generated control signals to control the operations of and the timing of various circuits in the processor 200 so as to perform processing suited to the electronic endoscope that is connected to the processor 200.

A timing controller 204 supplies a clock pulse to the driver signal processing circuit 112 in accordance with timing control performed by the system controller 202. In accordance with the clock pulse supplied from the timing controller 204, the driver signal processing circuit 112 controls the driving of the solid-state image sensor 108 according to a timing synchronized with the frame rate of the images processed by the processor 200.

Operations in Normal Mode

The following describes signal processing operations in the processor 200 in the normal mode.

The signal processing circuit 220 included in the processor 200 has a pre-process circuit 220A, a process circuit 220B, an output circuit 220C, a correction circuit 220D, a scoring circuit 220E, and a mapping circuit 220F.

The pre-process circuit 220A performs demosaic processing on RAW pixel data received from the driver signal processing circuit 112 at the frame cycle, performs conversion into RGB pixel data, performs color matrix processing, white balance adjustment, hue gain adjustment, and the like, and outputs the resulting pixel data to the process circuit 220B.

The process circuit 220B performs enhance processing, gamma correction, and the like on pixel data received from the pre-process circuit 220A, generates normal color image data, and outputs the image data to the output circuit 220C.

The output circuit 220C performs processing such as Y/C separation and color difference correction on the color image data received from the process circuit 220B, and performs conversion into a predetermined video format signal. The converted video format signal is output to the monitor 300. Accordingly, normal color images of the biological tissue are displayed on the display screen of the monitor 300.

Operations in Special Mode

Figure 2:
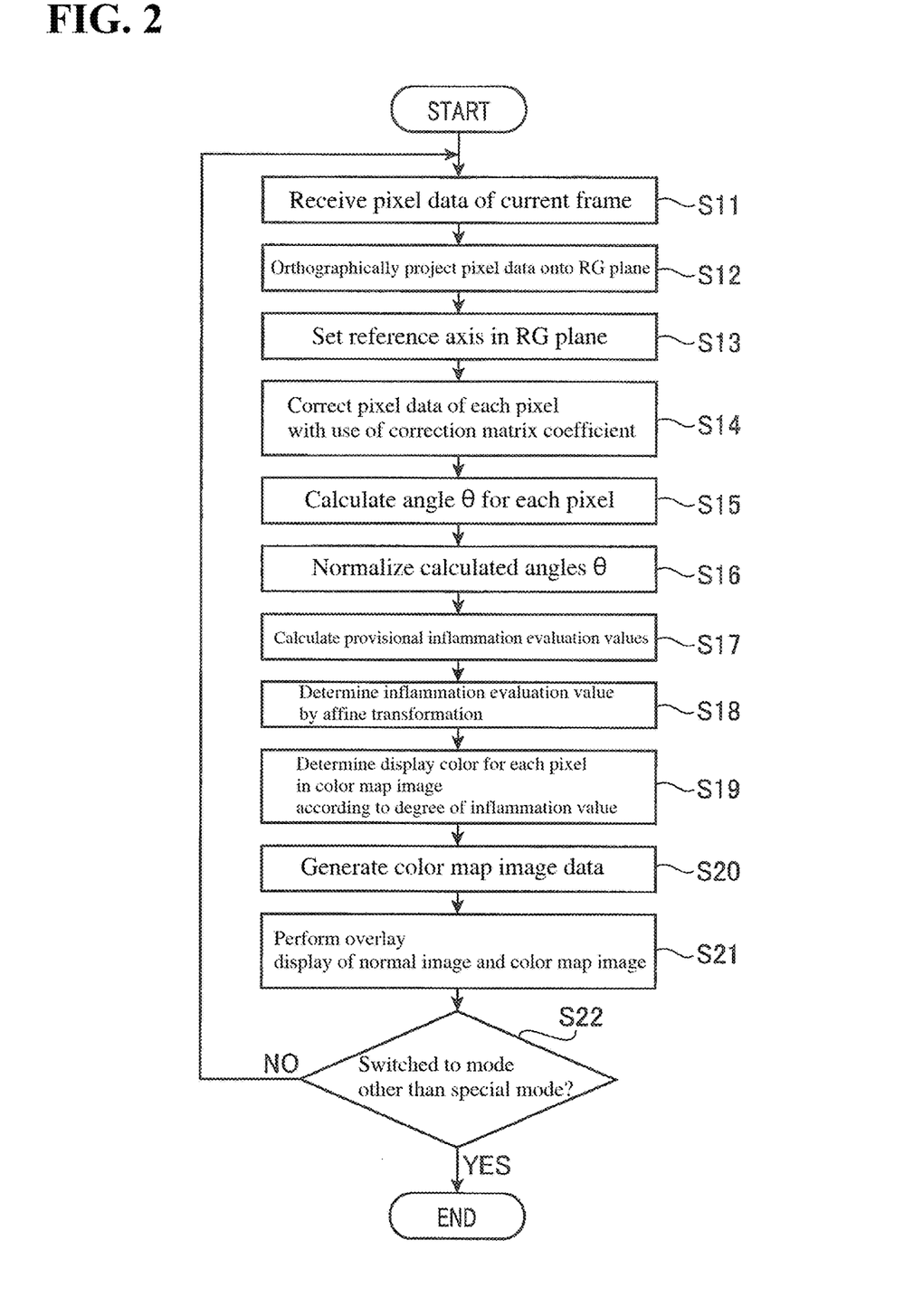
FIG. 2 is a diagram showing a flowchart of special image generation processing that is executed when in a special mode in an embodiment of the present disclosure.

Next, signal processing operations in the processor 200 in the special mode will be described. FIG. 2 shows a flowchart of special image generation processing executed in the special mode. The special image generation processing in FIG. 2 is started at the time when the operating mode of the electronic endoscope system 1 is switched to the special mode.

S11 (Input of Pixel Data of Current Frame) in FIG. 2

In this processing step S11, pixel data for each pixel of the current frame is input to the pre-process circuit 220A. The pixel data for each pixel is subjected to signal processing by the pre-process circuit 220A and then input to the process circuit 220B and the correction circuit 220D.

S12 (Orthographic Projecting onto RG Plane) in FIG. 2

Figure 3:
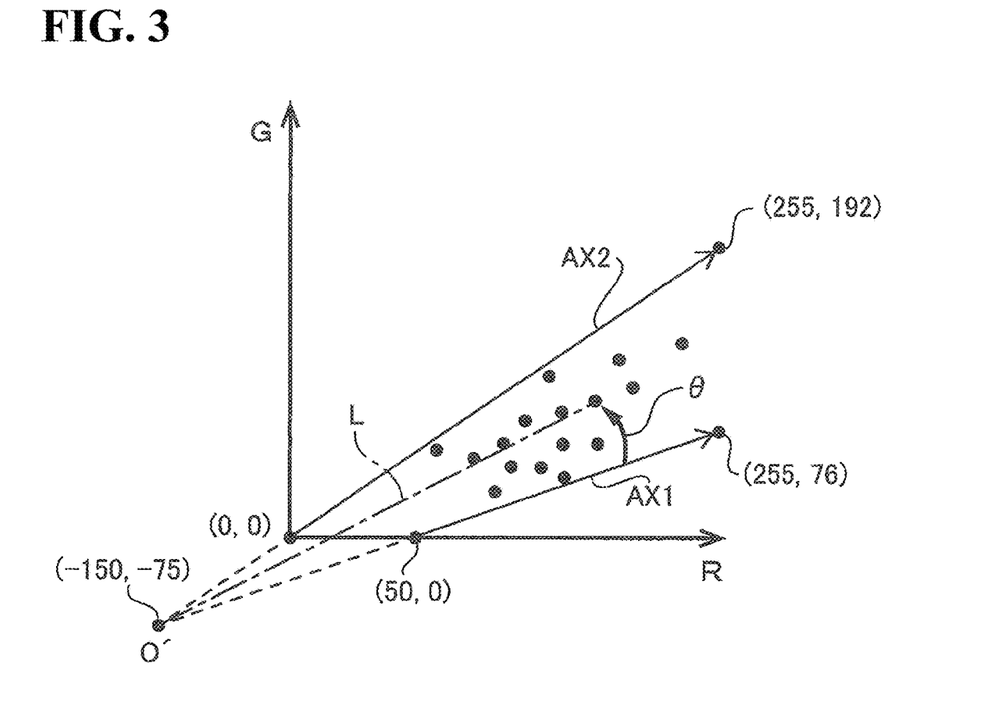
FIG. 3 is a diagram showing an RG plane in which pixel correspondence points are plotted in an embodiment of the present disclosure.

FIG. 3 is a diagram for conceptually illustrating operations of the correction circuit 220D, and shows an RG plane defined by an R axis and a G axis that are orthogonal to each other. Note that the R axis is the axis for the R component (R pixel values), and the G axis is the axis for the G component (G pixel values).

In this processing step S12, for each pixel, pixel data in the RGB color space defined by the three primary colors RGB (three-dimensional pixel data constituted by three types of color component) is converted into RG pixel data (two-dimensional pixel data constituted by two types of color components). As conceptually shown in FIG. 3, the pixel data for each pixel in the RGB color space is plotted on the RG plane according to the R and G pixel values (more specifically, is plotted in a section of the RG plane that takes the values of R=0 to 255 and G=0 to 255). Hereinafter, for the sake of convenience in the description, the points corresponding to the pixel data of pixels in the RGB color space and the points corresponding to the pixel data plotted on the RG plane will be referred to as "pixel correspondence points". Note that for the sake of clarity in FIG. 3, pixel correspondence points are shown for only some pixels rather than for all of the pixels.

Note that in the present disclosure, the color components constitute the color space (including the color plane as well). Also, hue and saturation are excluded from the term "color component".

In this way, in this processing step S12, pieces of pixel data in the RGB color space (three-dimensional data) are orthographically projected onto the RG plane, such that for each piece of pixel data, the foot of a vertical line extending from the corresponding point in the RGB color space down to the RG plane is considered to the pixel correspondence point (two-dimensional data).

Note that the operation by which the pixel data of pixels in the RGB color space is converted into pixel data in the RG plane (i.e., orthographic projection), which is performed in this processing step S12, is performed by a converting means. According to one embodiment, it is preferable that the correction circuit 220D shown in FIG. 2 handles the functions of the converting means.

S13 (Setting of Reference Axis) in FIG. 2

Figure 4:
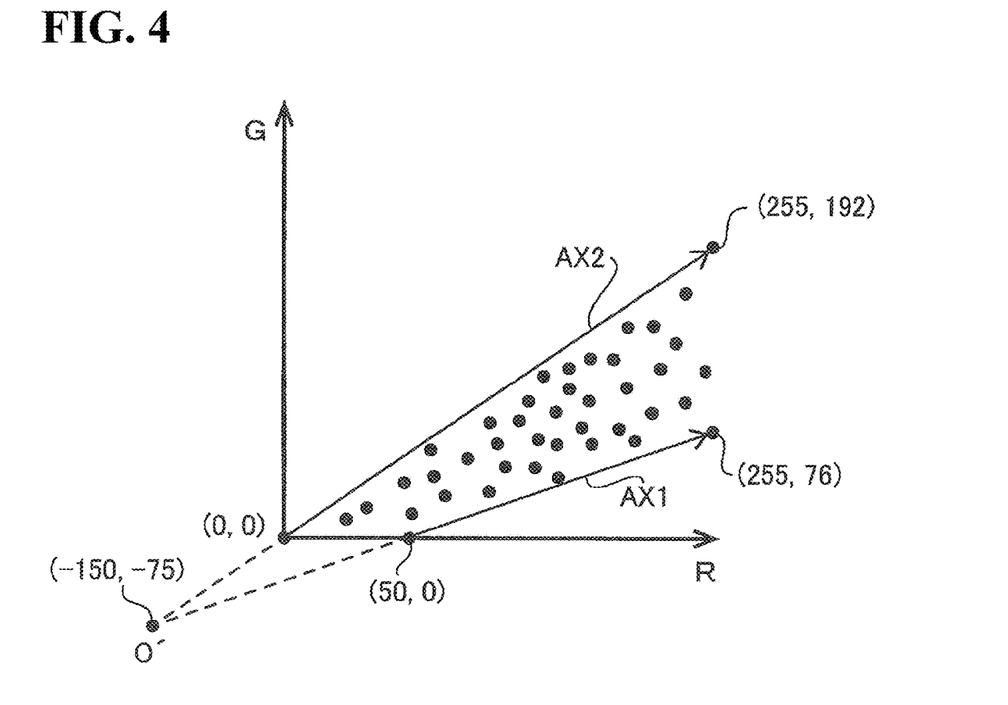
FIG. 4 is a diagram illustrating reference axes that are set in the RG plane.

In this processing step S13, a reference axis necessary for calculating the degree of inflammation of a target illness such as gastritis is set in the RG plane by the correction circuit 220D. FIG. 4 shows a diagram for assisting the description of the reference axis.

Due to influences such as hemoglobin pigment, the R component is dominant over the other components (G component and B component) in biological tissue in the body cavity of the patient that is to be imaged, and the more intense the inflammation is, the redness (R component) typically increases relative to the other hues (G component and B component). However, in images of biological tissue captured inside a body cavity, the hue varies according to imaging conditions that influence brightness (e.g., degree of illumination with white light L). For example, shaded portions not reached by the white light L appear black (achromatic, with R, G, and B values at or near zero, for example), and portions where the white light L strikes intensely and is specularly reflected appear white (achromatic, with R, G, and B values at or near 255). In other words, even when the same inflamed abnormal site is imaged, the pixel value in the image of the abnormal site will be higher the more intensely the white light L strikes it. For this reason, depending on the degree of illumination with the white light L, the pixel value may take a value that has no correlation with the degree of inflammation.

Generally, normal sites inside a body cavity that are not inflamed are sufficiently covered by a mucous membrane. In contrast, abnormal sites inside a body cavity that are inflamed are not sufficiently covered by a mucous membrane. Specifically, when a blood vessel expands, blood and body fluids leak from the blood vessel, and therefore the mucous membrane becomes relatively thinner, and the color of blood becomes more easily visible. A mucous membrane is basically white in color, but has a slightly yellowish hue, and the hue (yellow hue) that appears in an image varies according to the darkness/lightness (membrane thickness). Accordingly, the darkness/lightness of the mucous membrane is also thought to be an evaluation determination reference for evaluating the degree of inflammation.

In view of this, in this processing step S13, as shown in FIG. 4, a straight line that passes through (50,0) and (255,76) in the RG plane is set as one reference axis, and a straight line that passes through (0,0) and (255,192) is set as one reference axis. For the sake of convenience in the description, the former reference axis will be called the "hemoglobin variation axis AX1", and the latter reference axis will be called the "mucous membrane variation axis AX2".

The plot shown in FIG. 4 is the result of the inventor of the present disclosure analyzing a large number of sample images of biological tissue in body cavities. The sample images used in the analysis included examples of images of various stages of inflammation, including examples of images of inflammation of the highest symptom level (examples of images of inflammation of the most severe level) and examples of images of inflammation of the lowest symptom level (examples of images deemed to be substantially normal sites or healthy sites). Note that for the sake of clarity in the diagram, only a portion of the points obtained as analysis results is shown in the example in FIG. 4. The actual points obtained as analysis results are much higher in number than the number of points shown in FIG. 4.

As described above, the higher the degree of inflammation at an abnormal site is, the more intense the R component is relative to the other components (G component and B component). For this reason, an axis on the boundary line that separates regions where points are distributed and are not distributed, and that is closer to the R axis than the G axis, which is the boundary line that passes through (50,0) and (255,76) in the example in FIG. 4, is set as the axis having a high correlation with a lesion site that has the highest symptom level (an inflamed site (abnormal site) with the highest symptom level). This axis is the hemoglobin variation axis AX1. Plotted points that correspond to inflamed sites that have the highest symptom level and were imaged under various imaging conditions, such as degree of illumination with the white light L, are overlapped with the hemoglobin variation axis AX1.

On the other hand, the lower the extent of inflammation, and the closer a site approximates a normal site, the more intense the G component (or the B component) is relative to the R component. For this reason, an axis on the boundary line that separates regions where plotted points are distributed and are not distributed, and that is closer to the G axis than the R axis, which is the boundary line that passes through (0,0) and (255,192) in the example in FIG. 4, is set as the axis having a high correlation with a lesion site with the lowest symptom level (an inflamed site (abnormal site) with the lowest symptom level, which is deemed to be a substantially normal site, or in other words healthy site). This axis is the mucous membrane variation axis AX2. Plotted points that correspond to inflamed sites that have the lowest symptom level (i.e., sites deemed to be substantially normal sites) and were imaged under various imaging conditions, such as degree of illumination with the white light L, are overlapped with the mucous membrane variation axis AX2.

To give a further description, an inflamed site with the highest symptom level for a target illness is accompanied by bleeding. On the other hand, an inflamed site with the lowest symptom level is a substantially normal site, and therefore is covered by a sufficient mucous membrane. For this reason, it can be understood that the points in the RG plane shown in FIG. 4 are distributed in the region sandwiched between the axis that has the highest correlation with blood (hemoglobin pigment) and the axis that has the highest correlation with the hue of the mucous membrane. For this reason, out of the boundary lines that separate regions where plotted points are distributed and are not distributed, the boundary line closer to the R axis (higher R component) corresponds to the axis that indicates an inflamed site with the highest symptom level, that is to say the hemoglobin variation axis AX1, and the boundary line closer to the G axis (higher G component) corresponds to the axis that indicates an inflamed site with the lowest symptom level, that is to say the mucous membrane variation axis AX2.

S14 (Correction of Pixel Data) in FIG. 2

A correction matrix coefficient that is calculated in the later-described calibration mode is stored in a storage medium such as a memory in the correction circuit 220D or the memory 222. In this processing step S14, in order to suppress variation in score values when the same lesion site is imaged with different electronic endoscope systems, or in other words in order to suppress individual differences between electronic endoscopes, the pixel data (R, G) at the pixel correspondence point of each pixel is corrected by the correction circuit 220D with use of a correction matrix coefficient.

Example of Correction Matrix $$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: corrected pixel data (R component)
$G_{new}$: corrected pixel data (G component)
$M_{00}$-$M_{11}$: correction matrix coefficient
R: uncorrected pixel data (R component)
G: uncorrected pixel data (G component)

Note that the operation of correcting the pixel correspondence point of each pixel with use of a correction matrix coefficient, which is executed in this processing step S14, is performed by a color component correcting means. According to one embodiment, it is preferable that the correction circuit 220D shown in FIG. 2 handles the functions of the color component correcting means.

S15 (Calculation of Angle) in FIG. 2

In this processing step S15, an angle for calculating a degree of inflammation is calculated for the pixel data ($R_{new}$, $G_{new}$) of each pixel in the current frame that was obtained by the correction performed by the correction circuit 220D in the processing step S14 (color correction of pixel data). Specifically, this processing step S15 is processing for calculating, for each pixel, an angle θ formed by the hemoglobin variation axis AX1 and a line segment L that connects the pixel correspondence point ($R_{new}$, $G_{new}$) and an intersection (reference point) O' of the hemoglobin variation axis AX1 and the mucous membrane variation axis AX2 (see FIG. 3). Note that the reference point O' is located at the coordinates (−150,−75).

S16 (Normalization Processing) in FIG. 2

When the brightness of the captured image of biological tissue in a body cavity changes according to the degree of illumination with the white light L, the hue of the captured image is influenced by individual differences, the imaged location, the state of inflammation, and the like, but in the RG plane, the hue changes approximately along the hemoglobin variation axis AX1 at an inflamed site with the highest symptom level, and the hue changes approximately along the mucous membrane variation axis AX2 at an inflamed site with the lowest symptom level, that is to say a healthy site. It is also inferred that the hue of the captured image at an inflamed site with a moderate symptom level also changes with the same tendency. Specifically, when a pixel correspondence point corresponding to an inflamed site changes according to the degree of illumination with the white light L, a shift occurs in the azimuth angle direction with the reference point O' serving as the origin. In other words, when a pixel correspondence point corresponding to an inflamed site changes according to the degree of illumination with the white light L, the distance from the reference point O' changes while the angle θ remains constant. This means that the angle θ is a parameter that is substantially not influenced by change in the brightness of the captured image.

The lower the angle θ is, the more intense the R component is relative to the G component, which indicates that the symptom level of the inflamed site is higher. Also, the higher the angle θ is, the more intense the G component is relative to the R component, which indicates that the symptom level of the inflamed site is lower.

In view of this, in this processing step S16, for all of the pixels in the current frame, the scoring circuit 220E normalizes the angle θ so as to take a value of 255 when the angle θ is zero and take a value of zero when the angle θ is $θ_{MAX}$. Note that $θ_{MAX}$ is equivalent to the angle formed by the hemoglobin variation axis AX1 and the mucous membrane variation axis AX2. This therefore obtains information indicating a degree of inflammation that falls within the range of 0 to 255, that is to say 8-bit information.

S17 (Calculation of Inflammation Evaluation Value) in FIG. 2

In this processing step S17, the scoring circuit 220E calculates the average value of the degree of inflammation of all of the pixels in the current frame, or calculates an integrated value of the degree of inflammation of all of the pixels, as a provisional inflammation evaluation value of the overall captured image.

Note that the operation of calculating the inflammation evaluation value, which is executed in this processing step S17, is performed by an acquiring means. According to one embodiment, it is preferable that the scoring circuit 220E shown in FIG. 2 handles the functions of the acquiring means.

S18 (Determination of Inflammation Evaluation Value) in FIG. 2

Affine transformation coefficients α and β that are calculated in the later-described calibration mode are stored in a storage medium such as a memory in the correction circuit 220D or the memory 222. In this processing step S18, in order to suppress variation in score values when the same lesion site is imaged with different electronic endoscope systems, or in other words in order to suppress individual differences between electronic endoscopes, the provisional inflammation evaluation value that was calculated in the processing step S17 (calculation of inflammation evaluation value) is subjected to affine transformation using the affine transformation coefficients α and β to obtain a definitive value, as shown in the following expression. Also, in this processing step S18, display data for the inflammation evaluation value that was transformed into a definitive value (example of display data: Score: OO) is generated.

Example of Affine Transformation $$H=αH'+β$$

H: inflammation evaluation value (definitive value)
H': inflammation evaluation value (provisional value)

The following illustrates a method for calculating the affine transformation coefficients α and β. When calculating the affine transformation coefficients α and β, a provisional inflammation evaluation value (hereinafter, called a "sample inflammation evaluation value" for the sake of convenience in the description) is calculated for multiple sample images. A coefficient set (slope α, intercept β) for transforming the highest one of the calculated sample inflammation evaluation values to a first specified value, for example the maximum value among the inflammation evaluation values, and for transforming the lowest sample inflammation evaluation value to a second specified value that is lower than the first specified value, for example the minimum value among the inflammation evaluation values, is obtained as the affine transformation coefficients.

Note that various coefficients are conceivable as the affine transformation coefficients α and β. For example, the affine transformation coefficients α and β may be a coefficient set for transforming the average value of all of the calculated sample inflammation evaluation values to a specified value, or a coefficient set for minimizing the sum of the differences between a predetermined target value and the respective sample inflammation evaluation values.

Note that the operation of performing affine transformation on the inflammation evaluation values using the affine transformation coefficients α and β, which is executed in this processing step S18, is performed by an evaluation result correcting means. According to one embodiment, it is preferable that the scoring circuit 220E shown in FIG. 2 handles the functions of the evaluation result correcting means.

S19 (Determination of Display Color in Color Map Image) in FIG. 2

In the present embodiment, it is possible to display a color map image in which a captured image is displayed in a mosaic form with display colors that correspond to the degree of inflammation. In order to enable the display of a color map image, a table of correspondence between degree of inflammation values and predetermined display colors is stored in a predetermined storage region in the scoring circuit 220E. In this table, different display colors are associated with each range of five values, for example. For example, yellow is associated with the range of degree of inflammation values 0 to 5, different display colors are associated with successive groups of five higher values according to the color order in the hue circle, and red is associated with the range of values 250 to 255.

In this processing step S19, the display color in the color map image for each pixel in the current frame is determined by the mapping circuit 220F to be, based on the above-described table, the color that corresponds to the value of the degree of inflammation that was obtained in S17 (calculation of inflammation evaluation value).

S20 (Generation of Color Map Image Data) in FIG. 2

In this processing step S20, the mapping circuit 220F converts the color data of each pixel in the current frame into data for the display color that was determined in processing step S19 (determination of display color in color map image), and generates color map image data that is made up of pixels to be displayed in the converted display colors.

Note that the operation of generating the color map image data, which is executed in this processing step S20, is performed by an acquiring means. According to one embodiment, it is preferable that the mapping circuit 220F shown in FIG. 2 handles the functions of the color map image acquiring means.

S21 (Overlay Processing) in FIG. 2

In this processing step S21, the output circuit 220C sets a coefficient as the ratio for overlaying a normal color image, which is based on normal color image data received from the process circuit 220B, and a color map image, which is based on color map image data generated in processing step S20 (generation of color map image data), and adds the former image data (normal color image data) and the latter image data (color map image data) based on the coefficient.

Note that the setting of the coefficient can be appropriately changed by a user operation. For example, in the case of a desire to display the normal color image more, the coefficient for the color image data is set higher, and in the case of a desire to display the color map image more, the coefficient for the color map image data is set higher.

S22 (End Determination) in FIG. 2

In this processing step S22, it is determined whether or not the operating mode of the electronic endoscope system 1 has been switched to a mode other than the special mode. If it is determined that the operating mode has not been switched to another mode (S22: NO), the procedure in the special image generation processing in FIG. 2 returns to processing step S11 (input of pixel data of current frame). However, if it is determined that the operating mode has been switched to another mode (S22: YES), the special image generation processing in FIG. 2 ends.

Screen Display Example

The output circuit 220C generates display data for an overlay image including the normal color image and the color map image based on the image data obtained by the addition processing in processing step S21 (overlay processing) in FIG. 2, performs masking processing for masking the peripheral region of the display screen of the monitor 300 (periphery of the image display region), and furthermore generates monitor display screen data in which the inflammation evaluation value is superimposed on the mask region generated by the masking processing. The output circuit 220C converts the generated monitor display screen data into a predetermined video format signal, and outputs the signal to the monitor 300.

Figure 5:
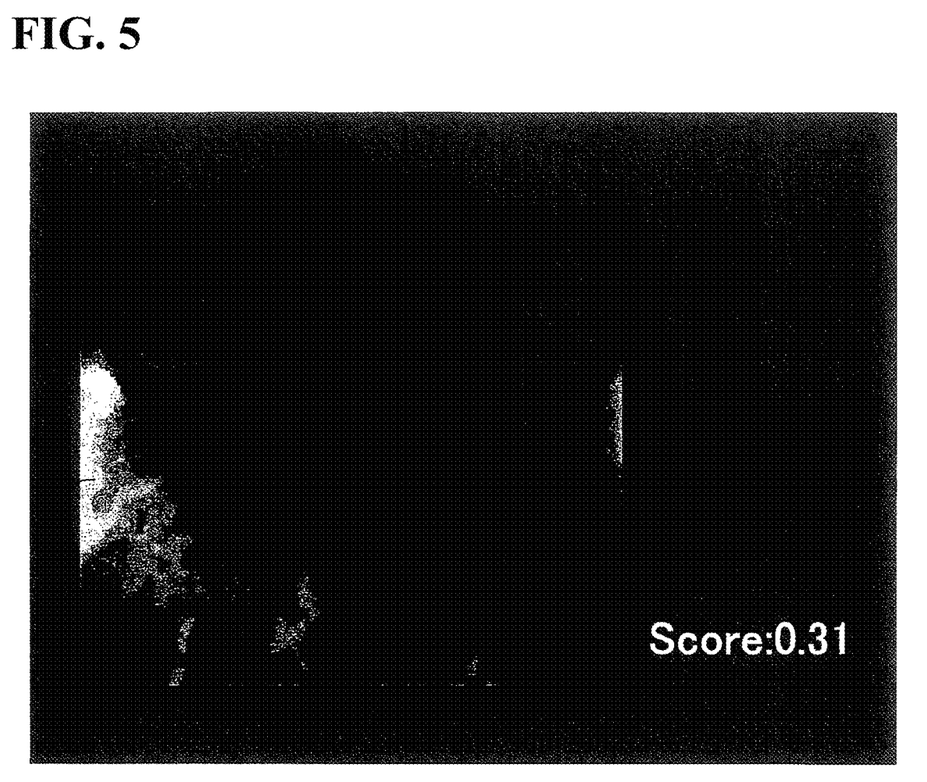
FIG. 5 is a diagram showing an example of a display screen that is displayed on a display screen of a monitor when in the special mode in an embodiment of the present disclosure.

FIG. 5 shows an example of screen display in the special mode. As shown in FIG. 5, the display screen of the monitor 300 includes the intracavitary captured image (overlay image in which the normal image and the color map image are overlaid) in the central region, and a masked screen region surrounding the image display region. The inflammation evaluation value (score) is also displayed in the mask region.

Note that the mode of display of the captured image in the special mode is not limited to being overlay display of a normal color image and a color map image. For example, there are also display modes such as arranging the normal color image and the color map image side-by-side in the same screen, and displaying only the color map image. In the former case, the normal color image and the color map image may both be displayed at the same size, or a configuration is possible in which either the normal color image or the color map image is displayed as the main image, and the other one is displayed as a sub image that is smaller than the main image.

The operation of displaying an imaging including the inflammation evaluation value and the color map image on the display screen of the monitor 300, which is executed by the output circuit 220C, is performed by a displaying means. According to one embodiment, it is preferable that the output circuit 220C shown in FIG. 2 handles the functions of the displaying means.

In this way, according to the embodiment, a precise inflammation evaluation value and color map image are obtained by merely performing simple calculation processing, and without performing nonlinear calculation processing such as tone enhancement processing, or complicated color space conversion processing, or the like. In other words, the amount of hardware resources needed for inflammation evaluation value calculation and color map image generation is significantly suppressed.

Also, according to the embodiment, the inflammation evaluation value and the color map image substantially do not vary depending on imaging conditions that influence the brightness of the captured image in the body cavity, such as the degree of illumination with irradiation light. For this reason, the operator can precisely identify lesion sites or the like, and can more objectively make an accurate diagnosis.

Operations in Calibration Mode

Next, operations of the electronic endoscope system 1 in the calibration mode will be described. In calibration processing that is executed when in the calibration mode, calibration is performed for correcting a specific color that is related to a target illness.

Figure 6:
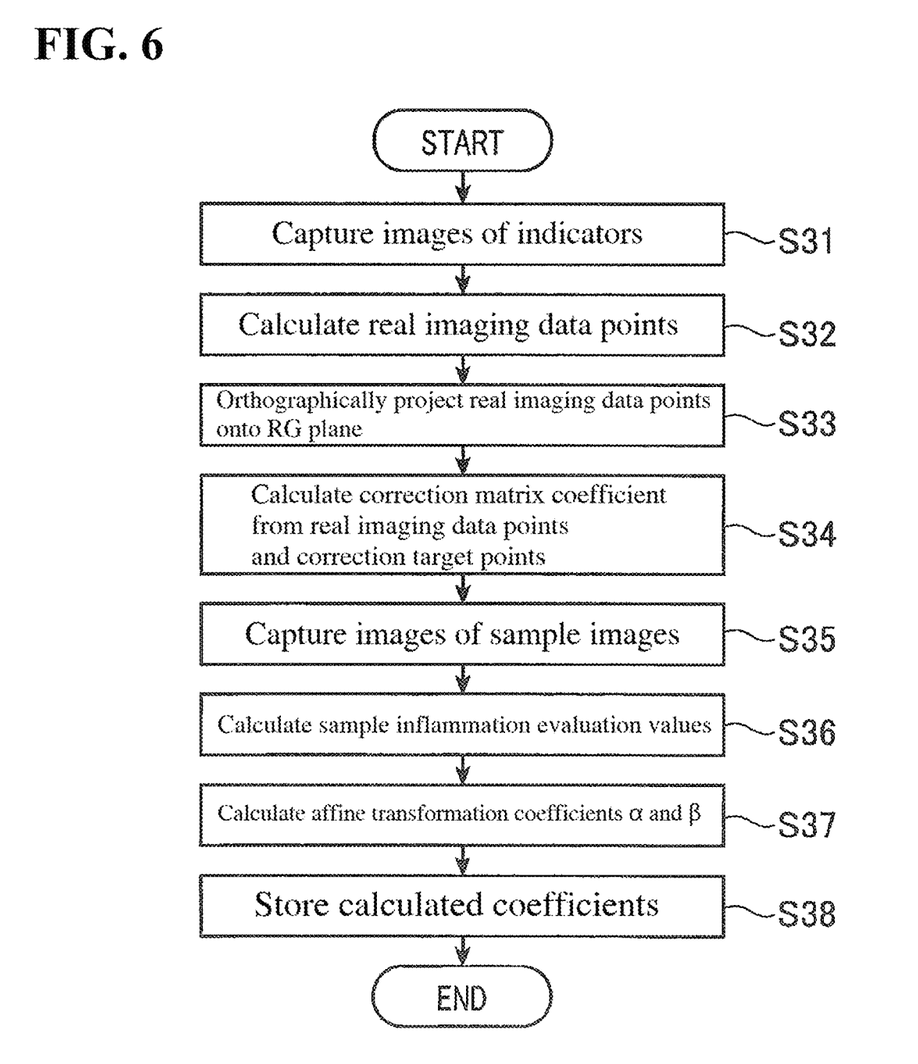
FIG. 6 is a diagram showing a flowchart of calibration processing that is executed when in a calibration mode in an embodiment of the present disclosure.

FIG. 6 shows a flowchart of calibration processing executed in the calibration mode. The calibration processing in FIG. 6 is executed at the time of factory shipment or maintenance for example, and is started when the operating mode of the electronic endoscope system 1 is switched to the calibration mode.

Note that preparation operations may be performed by a worker prior to the execution of calibration processing. Specifically, the worker adjusts the white balance of the electronic endoscope system 1 with use of a white balance dedicated jig, or a white board, a gray card, or the like that has the same specifications as the white balance dedicated jig.

When white balance adjustment is complete, the worker sets the electronic endoscope system 1 in a calibration jig and starts calibration software on an electronic endoscope system terminal (PC) that is connected to the processor 200.

The worker then performs luminance adjustment on a captured image captured by the electronic endoscope 100. For example, the worker manually adjusts the aperture of the diaphragm 212 such that the luminance value of a captured image, which is obtained by imaging a subject for luminance adjustment, coincides with a target luminance value. Note that the luminance value of the captured image can be checked with the calibration software.

Figure 7:
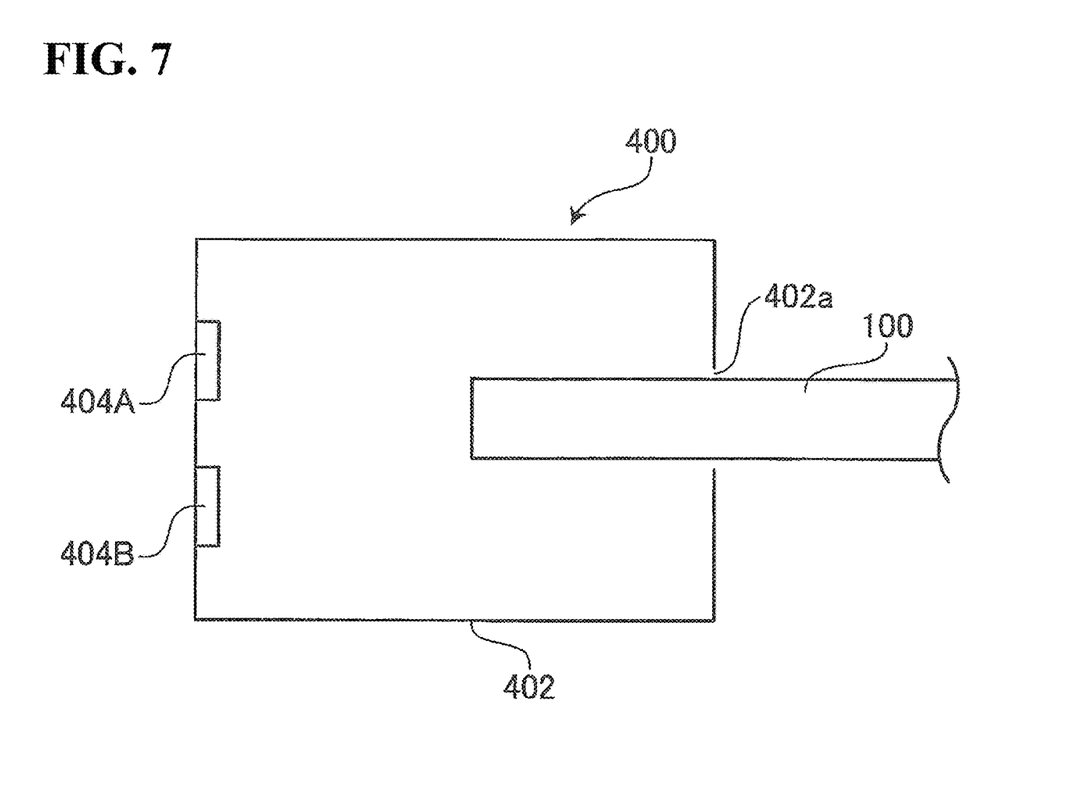
FIG. 7 is a diagram showing a schematic configuration of a calibration jig according to an embodiment of the present disclosure.

FIG. 7 shows the schematic configuration of a calibration jig 400 according to the present embodiment. As shown in FIG. 7, the calibration jig 400 includes a measurement box 402. An introduction opening 402a is formed in the measurement box 402.

The worker inserts the distal end portion of the electronic endoscope 100 through the introduction opening 402a to a predetermined position in the measurement box 402. The introduction opening 402a is substantially closed due to the distal end portion of the electronic endoscope 100 being inserted into the measurement box 402. Accordingly, external light does not enter the measurement box 402, and the measurement box 402 functions as a black box. Calibration precision improves because there is no influence from external light when calibration processing is performed.

Inside the measurement box 402, a pair of indicators (specified color samples) 404A and 404B are set at positions opposing the introduction opening 402a, or in other words positions that face the leading end face (face provided with the light distribution lens, objective lens, and the like) of the electronic endoscope 100. The indicators (specified color samples) are color indicators that simulate specific colors that are related to a target illness, and can be replaced as necessary according to the target illness.

The indicator (specified color sample) 404A is an indicator that simulates a first color that is the color of biological tissue when the symptom level of a target illness is the highest, for example. In the present embodiment, the indicator 404A is a plate-shaped member that is painted with a color that corresponds to a predetermined point (a later-described correction target point PT1) on the hemoglobin variation axis AX1 in the RG plane.

The indicator (specified color sample) 404B is an indicator that simulates a second color that is the color of healthy biological tissue, for example. In this embodiment, the indicator 404B is a plate-shaped member that is painted with a color that corresponds to a predetermined point (a later-described correction target point PT2) on the mucous membrane variation axis AX2 in the RG plane.

S31 (Imaging of Indicator) in FIG. 6

While viewing the captured image displayed on the display screen of the monitor 300, the worker adjusts the position of the distal end portion of the electronic endoscope 100 in the measurement box 402 such that the indicators 404A and 404B fit in the angle of view of the electronic endoscope 100. In this processing step S31, an image of the indicators 404A and 404B in the angle of view is captured by the electronic endoscope 100 in accordance with an operation input by the worker, and that captured image data is input to the processor 200. Note that images of the indicators 404A and 404B may be captured separately. By using the calibration jig 400, the worker can capture an image of the indicator 404A and the indicator 404B under the same conditions.

S32 (Calculation of Real Imaging Data Point P) in FIG. 6

Execution of this processing step S32 is started in accordance with operation input from the worker or automatically after the capture of a designated number of images (here, one image).

In this processing step S32, the calibration software calculates real imaging data points $P_{D1}$ and $P_{D2}$ as the real measurement values of the indicators 404A and 404B based on the captured image data that was captured in the processing step S31 (imaging of indicators). For example, the average value of pixels (e.g., 200×200 pixels) in the central region of the image of the indicator 404A extracted from the captured image is calculated as the real imaging data point $P_{D1}$, and the average value of pixels (e.g., 200×200 pixels) in the central region of the image of the indicator 404B extracted from the captured image is calculated as the real imaging data point $P_{D2}$.

S33 (Orthographic Projection of Real Imaging Data Points onto RG Plane) in FIG. 6

In this processing step S33, the calibration software orthographically projects the real imaging data point $P_{D1}$ ($R_{D1}$,$G_{D1}$,$B_{D1}$) and the real imaging data point $P_{D2}$($R_{D2}$, $G_{D2}$,$B_{D2}$) in the RGB color space onto the RG plane that is associated with a target illness for conversion into a real imaging data point $P_{D1}$($R_{D1}$,$G_{D1}$) and a real imaging data point $P_{D2}$($R_{D2}$,$G_{D2}$).

S34 (Calculation of Correction Matrix Coefficient) in FIG. 6

In this processing step S34, a correction matrix coefficient is calculated by the calibration software. As shown in the following expression, the correction matrix coefficient is a coefficient for correcting measurement values, that is to say the real imaging data point $P_{D1}$($R_{D1}$,$G_{D1}$) and the real imaging data point $P_{D2}$($R_{D2}$,$G_{D2}$), into target values, that is to say a correction target point $P_{T1}$($R_{T1}$,$G_{T1}$) and a correction target point $P_{T2}$($R_{T2}$,$G_{T2}$). Note that the correction target point $P_{T1}$($R_{T1}$,$G_{T1}$) corresponds to the color on the hemoglobin variation axis AX1 that is simulated by the indicator 404A, and the correction target point $P_{T2}$($R_{T2}$,$G_{T2}$) corresponds to the color on the mucous membrane variation axis AX2 that is simulated by the indicator 404B.

$$\begin{pmatrix} R_{T1} & R_{T2} \\ G_{T1} & G_{T2} \end{pmatrix} = \begin{pmatrix} M_{00} & M_{01} \\ M_{10} & M_{11} \end{pmatrix} \begin{pmatrix} R_{D1} & R_{D2} \\ G_{D1} & G_{D2} \end{pmatrix}$$

It can be understood from the above expression that the correction matrix coefficient is obtained by the following expression.

$$\begin{pmatrix} M_{00} & M_{01} \\ M_{10} & M_{11} \end{pmatrix} = \begin{pmatrix} R_{T1} & R_{T2} \\ G_{T1} & G_{T2} \end{pmatrix} \begin{pmatrix} R_{D1} & R_{D2} \\ G_{D1} & G_{D2} \end{pmatrix}^{-1}$$

Note that the operation of calculating the correction matrix coefficient, which is executed in this processing step S34, is performed by a color component correction coefficient calculating means. According to an embodiment, it is preferable that a software module in the electronic endoscope system terminal (PC) connected to the processor 200 handles the function of the color component correction coefficient calculating means.

S35 (Imaging of Sample Image) in FIG. 6

In this processing step S35, images of multiple sample images are captured using the electronic endoscope 100. Examples of the sample images include captured images of indicators (the indicators 404A and 404B or other indicators, for example) set in the measurement box 402, and images of indicators captured using a means other than the calibration jig 400.

S36 (Calculation of Sample Inflammation Evaluation Value) in FIG. 6

In this processing step S36, a sample inflammation evaluation value is calculated for each of the sample images that were imaged in the processing step S35 (imaging of sample image).

S37 (Calculation of Affine Transformation Coefficient) in FIG. 6

In this processing step S37, affine transformation coefficients α and β are calculated using the sample inflammation evaluation values that were calculated for the sample images in the processing step S36 (calculation of sample inflammation evaluation value). Note that the method for calculating the affine transformation coefficients α and β may be any of the methods described in the processing step S18 (determination of inflammation evaluation value) in FIG. 2, or may be another method.

Note that the operation of calculating the affine transformation coefficients α and β, which is executed in this processing step S37, is performed by an evaluation result correction coefficient calculating means. According to an embodiment, it is preferable that a software module in the electronic endoscope system terminal (PC) connected to the processor 200 handles the function of the evaluation result correction coefficient calculating means.

S38 (Storage of Coefficients) in FIG. 6

In this processing step S38, the correction matrix coefficient that was calculated in the processing step S34 (calculation of correction matrix coefficient) and the affine transformation coefficients α and β that were calculated in the processing step S37 (calculation of affine transformation coefficient) are stored in a storage medium such as a memory in the correction circuit 220D of the processor 200 or the memory 222. Accordingly, the calibration processing shown in FIG. 6 is complete.

By executing calibration processing on each electronic endoscope system, it is possible to obtain substantially the same evaluation results, that is to say the same inflammation evaluation value and the same color map image, when indicators related to a target illness are imaged by each electronic endoscope system. For this reason, it is possible to suppress variation in evaluation result even when images of a target illness are actually captured by each electronic endoscope system.

In other words, according to the embodiment, limiting the target of correction, or more specifically setting a specified color related to a target illness as the target of correction, favorably eliminates error that remains in color data used when evaluating the target illness, that is to say mainly error arising from variation caused by individual differences between optical components of the electronic endoscope 100. Evaluation precision therefore improves.

Also, according to another embodiment, the color components that are subjected to color correction using the correction matrix coefficient are only the m types of color components obtained by conversion from the n types of color components, and do not include (n-m) types of color components. The (n-m) types of color components are not used to obtain the inflammation evaluation value, and therefore do not need to be subjected to color correction. In this way, color correction is performed on only the color components that are used to obtain the inflammation evaluation value, and therefore the correction matrix coefficient can be precisely created based on the indicators.

Note that it is not essential that correction using the correction matrix coefficient and correction using the affine transformation coefficients are both carried out. Carrying out only one of such correction obtains an effect of suppressing variation in evaluation results when images of biological tissue having a target illness are captured by different electronic endoscope systems.

Also, the electronic endoscope system according to the present embodiment achieves effects and problem solutions such as the following in the applicable technical fields.

First, the electronic endoscope system according to the embodiment is a diagnostic aid for early discovery of an inflammatory illness.

Second, according to the configuration of the embodiment, it is possible to display a screen showing the extent of inflammation or enhance the image in a region in which inflammation is occurring, such that the operator can discover mild inflammation that is difficult to view. In particular, mild inflammation is difficult to distinguish from a normal site, and therefore the effects achieved by the configuration of the embodiment regarding the evaluation of mild inflammation are remarkable.

Third, according to the configuration of the embodiment, it is possible to provide the operator with an objective evaluation value as an evaluation of the degree of inflammation, thus making it possible to reduce differences in diagnoses among operators. In particular, there is a large advantage of being able to provide an operator having little experience with an objective evaluation value obtained by the configuration of the present embodiment.

Fourth, according to the configuration of the embodiment, the load of image processing is reduced, thus making it possible to perform real-time display of images of an inflamed site. This makes it possible to improve diagnosis precision.

Fifth, according to the configuration of the embodiment, the processing load of evaluation value calculation is reduced, thus making it possible to display a color map image (image showing degrees of inflammation) and a normal image side-by-side or in a composited manner without lag. For this reason, it is possible to display a color map image without extending the inspection time, thus making it possible to avoid an increase in the burden on the patient.

The site that is to be observed in the present embodiment is a respiratory organ or the like, or a digestive organ or the like, for example. Here, "respiratory organ or the like" includes the lungs, the ears, the nose, and the throat, for example. "Digestive organ or the like" includes the large intestine, the small intestine, the stomach, the duodenum, and the uterus, for example. The electronic endoscope system according to the embodiment is thought to have even more remarkable effects when the observation target is the large intestine. The following are specific reasons for this.

The large intestine is susceptible to diseases that can be evaluated using inflammation as a reference, and the advantage of discovering inflamed sites is greater than in the case of other organs. In particular, the inflammation evaluation value obtained by the present embodiment is effective as an evaluation determination reference for inflammatory bowel disease (IBD), which is typified by ulcerative colitis. A method of treatment has not been established for ulcerative colitis, and therefore using the electronic endoscope system having the configuration of the present embodiment is very effective in making an early diagnosis and suppressing the progression of the illness.

The large intestine is a narrower and longer organ than the stomach and the like, and the obtained images have greater depth and are darker as the depth increases. According to the configuration of the embodiment, it is possible to suppress variation in the evaluation value caused by changes in the brightness in the image. Accordingly, when the electronic endoscope system according to the present embodiment is applied to the observation of the large intestine, the effects of the present embodiment are remarkable. In other words, the electronic endoscope system according to the embodiment is preferably a respiratory organ electronic endoscope system or a digestive organ electronic endoscope system, and is more preferably a large intestine electronic endoscope system.

Also, although mild inflammation is generally difficult to diagnose, according to the configuration of the embodiment, by displaying the results of degree of inflammation evaluation on the screen for example, it is possible to avoid a situation in which the operator misses mild inflammation. In particular, in the case of mild inflammation, the determination criteria are not clear, and this is a factor that causes a large amount of individual differences between operators. In this regard as well, according to the configuration of the embodiment, it is possible to provide the operator with an objective evaluation value, thus making it possible to reduce variation in diagnoses caused by individual differences.

Note that the above-described configuration of the embodiment is applicable to the calculation of an evaluation value of not only the degree of inflammation, but also cancer, polyps, and various other lesions that are accompanied by a color change, and advantageous effects similar to those described above can be achieved in these other cases as well. In other words, the evaluation value of the embodiment is preferably an evaluation value for a lesion that is accompanied by a color change, and includes an evaluation value of at least any of inflammation, cancer, and polyps.

An illustrative embodiment of the present disclosure is described above. The embodiments of the present disclosure are not limited to the above description, and various changes can be made without departing from the scope of the technical idea of the present disclosure. For example, appropriate combinations of embodiments and the like explicitly given as examples in this specification and obvious embodiments and the like are also encompassed in embodiments of the present disclosure.

In the above embodiment, the worker selects a first color, which is the color of biological tissue when the symptom level of the target illness is the highest for example, as one indicator, and selects a second color, which is the color of biological tissue when healthy for example, as another indicator. For this reason, in the above embodiment, calibration is performed with higher precision the closer the colors are to the first color and the second color, that is to say the correction targets, in the color space. In other words, calibration precision is lower the farther the colors are from the correction targets in the color space, that is to say a color that is improbable with inflammation, such as light blue.

Accordingly, it is sufficient that the worker selects, as an indicator to be set in the calibration jig when in the calibration mode, an indicator that corresponds to the symptom level that is to be scored with particularly high precision using the electronic endoscope system 1. For example, in the case of a desire to score mild inflammation with high precision, the worker need only select, as the indicator, an indicator that simulates the color of biological tissue when mild inflammation has occurred.

Note that the more subdivided the provided indicators are, the more difficult it is for the operator to select an appropriate indicator. In view of this, the system controller 202 can perform control such that when an operation for designating a symptom level is received from the worker via a connected peripheral device (e.g., a keyboard), the indicator that corresponds to the designated symptom level is displayed on the display screen of the monitor 300 or notified by audio playback. Accordingly, the operator can accurately select an appropriate indicator from among multiple indicators.

Also, when calibration processing is performed, at least two indicators are necessary. In other words, calibration processing may be performed using three or more indicators.

Also, in the above embodiment, processing such as correction by the correction matrix coefficient, correction by the affine transformation coefficients, and inflammation evaluation value calculation is all performed on the RG plane, but some of the processing, such as correction by the correction matrix coefficient, may be performed in another color space such as the YUV color space.

Also, image processing that involves changing a color according to a user setting, such as TE (Tone Enhancement) processing, may be performed by the process circuit 220B. The appropriate values for coefficients such as the correction matrix coefficient and the affine transformation coefficients are different depending on whether or not image processing involves changing a color is performed. For this reason, various coefficients that are suited to the case of performing TE processing and various coefficients that are suited to the case of not performing TE processing may be stored in a storage medium such as a memory in the correction circuit 220D or the memory 222. In the case of performing TE processing, correction is performed using the former various coefficients, and in the case of not performing TE processing, correction is performed using the latter various coefficients.

In the above embodiment, RGB color space pixel data is converted into RG plane pixel data, and an inflammation evaluation value related to a target illness is calculated using the R component and the G component included in the converted pixel data, but in another embodiment, a configuration is possible in which instead of the RGB color space, pixel data in another color space (a color space defined by n (n≥3) types of color components) such as the CIE 1976 L*a*b* color space, the CIE LCh color space, the CIE 1976 L*u*v* color space, the HSB color space, the sRGB color space, the CMK color space, the CMYK color space, or the CMYG color space is converted into pixel data in a lower order color space (a color space defined by m (n>m≥2) types of color components), and that pixel data is used to perform evaluation that corresponds to each color space and is related to a different target illness (stomach atrophy, large intestine tumor, or the like) from the above embodiment. In this case, the correction matrix coefficient and the affine transformation coefficients are calculated using indicators and target points that are different from the above embodiment.

Various correction matrix coefficients and affine transformation coefficients corresponding to various target illnesses may be stored in the memory 222 of the processor 200 or in a memory in the correction circuit 220D. By switching the correction matrix coefficient and the affine transformation coefficients according to the illness that is to be diagnosed, it is possible to perform evaluation value calculation that is stable (has little variation due to individual differences) for the corresponding target illness.

Various types of light sources can be used as the light source used in the electronic endoscope system 1. However, a mode is also possible in which the type of light source is limited depending on the observation target of the electronic endoscope system 1 or the like (e.g., a laser type is excluded as the type of light source). Here, in the correction matrix coefficient and the affine transformation coefficients, the optimum value changes according to the spectral characteristics of the light source that is used. Accordingly, in the case where the processor 200 includes multiple types of light sources, or multiple types of external light sources are switched during use for example, correction matrix coefficients and affine transformation coefficients for corresponding types of light sources may be stored in the memory 222 of the processor 200 or a memory in the correction circuit 220D. It is therefore possible to suppress variation in the inflammation evaluation value and the like caused by the spectral characteristics of the light source that is used.

Also, in the above embodiment, the angle θ formed by the hemoglobin variation axis AX1 and a line segment L that connects the reference point O' and the pixel correspondence point of the pixel of interest is calculated, and the inflammation evaluation value is calculated based on the calculated angle θ, but the present disclosure is not limited to this. For example, a configuration is possible in which the angle formed by the line segment L and the mucous membrane variation axis AX2 is calculated, and the inflammation evaluation value is calculated based on this calculated angle. In this case, the lower the calculated angle is, the more intense the G component is relative to the R component, which indicates that the severity of the inflamed site is lower, and the higher the calculated angle is, the more intense the R component is relative to the G component, which indicates that the severity of the inflamed site is higher. For this reason, in the processing step S16 (normalization processing) in FIG. 2, the inflammation evaluation value is normalized so as to take a value of zero when the calculated angle is zero, and take a value of 255 when the calculated angle is $\theta_{MAX}$.

Also, in the above embodiment, the intersection of the hemoglobin variation axis AX1 and the mucous membrane variation axis AX2 is set as the reference point O' in order to minimize the influence that captured image brightness has on the inflammation evaluation value, but the present disclosure is not limited to this. For example, the origin (0,0) of the RG plane located on the mucous membrane variation axis AX2 may be set as the reference point O'. In this case, the minimum required reference axis is only one axis (the mucous membrane variation axis AX2), thus reducing the load in the special image generation processing in FIG. 2 and improving the processing speed.

Also, although the light source portion (including the lamp power supply igniter 206, the lamp 208, the condensing lens 210, the diaphragm 212, the motor 214, and the like) is integrated with the processor in the above embodiment, the light source portion may be provided as an apparatus that is separate from the processor.

Also, as described in the above embodiment, instead of a CCD image sensor, a CMOS image sensor may be used as the solid-state image sensor 108. In general, with a CMOS image sensor, the image tends to be overall darker than in the case of a CCD image sensor. Accordingly, with the configuration of the above embodiment, the advantageous effect of being able to suppress variation in the evaluation value caused by image brightness is even more remarkable in a situation where a CMOS image sensor is used as the solid-state image sensor.

In order to precisely make a diagnosis, it is preferable to obtain high-definition images. Accordingly, from the viewpoint of further improving diagnosis precision, the image resolution is preferably 1 million pixels or more, more preferably 2 million pixels or more, and further preferably 8 million pixels or more. The higher the resolution of the image is, the greater the load becomes in processing for calculating the above-described evaluation value for all of the pixels. However, according to the configuration of the above embodiment, it is possible to suppress the processing load in evaluation value calculation, and therefore the advantageous effect of the configuration of the embodiment is remarkable in the situation of processing a high-definition image.

Also, although all of the pixels in the image are subjected to processing in the above embodiment, pixels having a very high luminance, pixels having a very low luminance, or the like may be excluded from the subjects of processing. Specifically, the precision of the evaluation value can be improved by performing evaluation value calculation on only pixels determined to have a luminance in a predetermined reference luminance range.

REFERENCE SIGNS LIST

1 Electronic endoscope system
100 Electronic endoscope
102 LCB
104 Light distribution lens
106 Objective lens
108 Solid-state image sensor
112 Driver signal processing circuit
114 Memory
200 Processor
202 System controller
204 Timing controller
206 Lamp power supply igniter
208 Lamp
210 Condensing lens
212 Diaphragm
214 Motor
216 Driver
218 Operation panel
220 Signal processing circuit
220A Pre-process circuit
220B Process circuit
220C Output circuit
220D Correction circuit
220E Scoring circuit
220F Mapping circuit
222 Memory

The invention claimed is:

1. An electronic endoscope processor comprising:
a converting means for converting each of a plurality of pieces of pixel data from an image sensor that are made up of n types of color components and constitute a color image of a biological tissue in a body cavity into a piece of pixel data that is made up of m types of color components, n being a natural number greater than or equal to 3, m being a natural number greater than or equal to 2, and m being smaller than n;
a color component correcting means for correcting, with use of a predetermined color component correction coefficient, converted pieces of pixel data from the converting means made up of the m types of color components; and
an acquiring means for acquiring an evaluation result related to a target illness based on corrected pieces of pixel data made up of the m types of color components.

2. The electronic endoscope processor according to claim 1, wherein the m types of color components subjected to the correcting by the color component correcting means are among the n types of color components.

3. The electronic endoscope processor according to claim 1, wherein the acquiring means is for setting a reference direction that is related to the target illness and extends from a predetermined reference point in a color space defined by the m types of color components and, for each of a plurality of pixels of the color image, for acquiring the evaluation result related to the target illness based on an extent to which a direction from the reference point to a pixel correspondence point that corresponds to the converted piece of pixel data in the color space deviates from the reference direction.

4. The electronic endoscope processor according to claim 3, wherein the directions from the reference point to the pixel correspondence points converge to the reference direction as a symptom level of the target illness rises.

5. The electronic endoscope processor according to claim 1, further comprising an evaluation result correcting means for correcting the acquired evaluation result with use of a predetermined affine transformation coefficient that performs affine transformation on the acquired evaluation result.

6. An electronic endoscope processor comprising:
a converting means for converting each of a plurality of pieces of pixel data from an image sensor that are made up of n types of color components and constitute a color image of a biological tissue in a body cavity into a piece of pixel data that is made up of m types of color components, n being a natural number greater than or equal to 3, m being a natural number greater than or equal to 2, and m being smaller than n;
a color component correcting means for correcting, with use of a predetermined color component correction coefficient, converted pieces of pixel data from the converting means made up of the m types of color components;

an acquiring means for acquiring an evaluation result related to a target illness based on corrected pieces of pixel data from the color component correcting means; and an evaluation result correcting means for correcting the acquired evaluation result with use of a predetermined evaluation result correction coefficient, wherein the m types of color components subjected to the correcting by the color component correcting means are among the n types of color components.

7. The electronic endoscope processor according to claim 6, wherein the color component correction coefficient is a predetermined correction matrix coefficient that corrects the pieces of pixel data made up of m types of color components.

8. The electronic endoscope processor according to claim 6, wherein the evaluation result correction coefficient is an affine transformation coefficient that performs affine transformation on the acquired evaluation result.

9. The electronic endoscope processor according to claim 6, wherein the acquiring means is for setting a reference direction that is related to the target illness and extends from a predetermined reference point in a color space defined by the m types of color components and, for each of a plurality of pixels of the color image, for acquiring the evaluation result related to the target illness based on an extent to which a direction from the reference point to a pixel correspondence point that corresponds to the converted piece of pixel data in the color space deviates from the reference direction.

10. The electronic endoscope processor according to claim 6, wherein the acquiring means is for acquiring a reference axis that is related to the target illness and passes through a predetermined reference point in a color plane defined by the m types of color components and, for each of a plurality of pixels, for acquiring the evaluation result related to the target illness based on an angle $\theta$ formed by the reference axis and a line segment that connects the reference point and a pixel correspondence point corresponding to the piece of pixel data.

11. The electronic endoscope processor according to claim 10, wherein letting the reference axis be a first reference axis, the acquiring means is for setting a second reference axis that is related to a healthy site not having the target illness and that passes through the reference point in the color plane and for normalizing the angle $\theta$ with use of an intersecting angle of the first reference axis and the second reference axis as a maximum angle before the evaluation result is calculated.

12. The electronic endoscope processor according to claim 10, wherein the converting means is for orthographically projecting, onto the color plane, the pieces of pixel data in a color space defined by the n types of color components.

13. The electronic endoscope processor according to claim 10, wherein the reference axis is an axis to which the pixel correspondence points increasingly converge as a symptom level of the target illness rises.

14. The electronic endoscope processor according to claim 10, wherein the color plane is a plane that includes an R component axis and a G component axis.

15. The electronic endoscope processor according to claim 6, wherein the m types of color components of the converted pieces of pixel data are color components set so as to have mutually different wavelength bands.

16. The electronic endoscope processor according to claim 6, wherein the evaluation result includes at least one of a value indicating an evaluation related to the target illness, and a color image indicating an evaluation related to the target illness.

17. An electronic endoscope system comprising:
an electronic endoscope processor comprising:
a converting means for converting each of a plurality of pieces of pixel data from an image sensor that are made up of n types of color components and constitute a color image of a biological tissue in a body cavity into a piece of pixel data that is made up of m types of color components, n being a natural number greater than or equal to 3, m being a natural number greater than or equal to 2, and m being smaller than n;

a color component correcting means for correcting, with use of a predetermined color component correction coefficient, converted pieces of pixel data from the converting means made up of the m types of color components, wherein the m types of color components subjected to the correcting by the color component correcting means are among the n types of color components;

an acquiring means for acquiring an evaluation result related to a target illness based on corrected pieces of pixel data from the color component correcting means; and an evaluation result correcting means for correcting acquired evaluation result with use of a predetermined evaluation result correction coefficient; and a display apparatus configured to display, on a display screen, an evaluation result obtained by the electronic endoscope processor.

18. The electronic endoscope system according to claim 17, wherein the electronic endoscope processor comprises:
a color map image acquiring means for acquiring a color map image by converting colors of pixels of the color image into colors that correspond to the evaluation values calculated as the evaluation results of the pixels; and
a displaying means for displaying the color map image on the display screen of the display apparatus, and wherein the display apparatus is configured to display a representative value of the evaluation values and the color map image at the same time.

19. The electronic endoscope system according to claim 17, wherein the acquiring means is for setting a reference direction that is related to the target illness and extends from a predetermined reference point in a color space defined by the m types of color components and, for each of a plurality of pixels of the color image, for acquiring the evaluation result related to the target illness based on an extent to which a direction from the reference point to a pixel correspondence point that corresponds to the converted piece of pixel data in the color space deviates from the reference direction.

20. The electronic endoscope system according to claim 19, wherein the directions from the reference point to the pixel correspondence points converge to the reference direction as a symptom level of the target illness rises.

* * * * *